(12) United States Patent
Sagel et al.

(10) Patent No.: US 10,493,016 B2
(45) Date of Patent: *Dec. 3, 2019

(54) TOOTH WHITENING PRODUCT

(71) Applicant: The Procter & Gamble Company, Cincinnati, OH (US)

(72) Inventors: Paul Albert Sagel, Maineville, OH (US); Lan Ngoc Nguyen, West Chester, OH (US); Randy Purnell Washington, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 129 days.

This patent is subject to a terminal disclaimer.

(21) Appl. No.: 15/377,577

(22) Filed: Dec. 13, 2016

(65) Prior Publication Data

US 2017/0087079 A1   Mar. 30, 2017

Related U.S. Application Data

(63) Continuation of application No. 13/953,879, filed on Jul. 30, 2013, now Pat. No. 9,554,976, which is a continuation of application No. 10/820,590, filed on Apr. 8, 2004, now Pat. No. 8,524,200, which is a continuation-in-part of application No. 10/659,100, filed on Sep. 10, 2003.

(60) Provisional application No. 60/409,862, filed on Sep. 11, 2002.

(51) Int. Cl.
| | |
|---|---|
| *A61K 8/00* | (2006.01) |
| *A61Q 11/00* | (2006.01) |
| *A61K 8/22* | (2006.01) |
| *A61K 8/02* | (2006.01) |
| *A61K 6/00* | (2006.01) |
| *A61K 8/19* | (2006.01) |
| *A61K 8/86* | (2006.01) |
| *A61K 8/81* | (2006.01) |

(52) U.S. Cl.
CPC .............. *A61K 8/86* (2013.01); *A61K 8/0208* (2013.01); *A61K 8/19* (2013.01); *A61K 8/22* (2013.01); *A61K 8/8129* (2013.01); *A61Q 11/00* (2013.01); *A61K 2800/594* (2013.01)

(58) Field of Classification Search
CPC .......... A61K 8/0208; A61K 8/19; A61K 8/22; A61K 8/8129; A61K 8/86; A61K 2800/594; A61Q 11/00

See application file for complete search history.

(56) References Cited

U.S. PATENT DOCUMENTS

| | | |
|---|---|---|
| 1,979,119 A | 10/1934 | Radzinsky |
| 2,560,724 A | 7/1951 | Harrison |
| 2,835,628 A | 5/1958 | Saffir |
| 2,994,362 A | 8/1961 | Hall |
| 3,047,966 A | 8/1962 | Greenspan |
| 3,070,102 A | 12/1962 | MacDonald |
| 3,096,202 A | 7/1963 | De Groot Von Arx |
| 3,256,014 A | 6/1966 | Kelsey |
| 3,444,858 A | 5/1969 | Russell |
| 3,598,123 A | 8/1971 | Zaffaroni |
| 3,625,215 A | 12/1971 | Quisling |
| 3,640,741 A | 2/1972 | Etes |
| 3,657,413 A | 4/1972 | Rosenthal et al. |
| 3,659,928 A | 5/1972 | MacFarlane |
| 3,688,406 A | 9/1972 | Porter et al. |
| 3,711,182 A | 1/1973 | Jasgur |
| 3,729,839 A | 5/1973 | Bourdier |
| 3,754,332 A | 8/1973 | Warren |
| 3,784,390 A | 1/1974 | Hijiya |
| 3,844,286 A | 10/1974 | Cowen |
| 3,859,987 A | 1/1975 | Holstad |
| 3,902,509 A | 9/1975 | Tundermann et al. |
| 3,955,281 A | 5/1976 | Weitzman |
| 3,964,164 A | 6/1976 | Hesselgren |
| 3,972,995 A | 8/1976 | Tsuk |
| 3,998,215 A | 12/1976 | Anderson |
| 4,029,757 A | 6/1977 | Miodozeniec |
| 4,029,758 A | 6/1977 | Miodozeniec |
| 4,031,200 A | 6/1977 | Reif |
| 4,032,627 A | 6/1977 | Suchan |
| 4,072,551 A | 2/1978 | Dabal |
| 4,084,700 A | 4/1978 | Dunchock |
| 4,136,145 A | 1/1979 | Fuchs |
| 4,136,162 A | 1/1979 | Fuchs et al. |
| 4,138,314 A | 2/1979 | Patil et al. |
| 4,138,814 A | 2/1979 | Weitzman |
| 4,139,627 A | 2/1979 | Lane |
| 4,182,222 A | 1/1980 | Stahl |
| 4,211,330 A | 7/1980 | Strock |
| 4,232,334 A | 11/1980 | Dyson |
| 4,251,400 A | 2/1981 | Columbus |
| 4,273,418 A | 6/1981 | Gillespie et al. |
| 4,292,299 A | 9/1981 | Suzuki |
| 4,294,820 A | 10/1981 | Keith |
| 4,307,075 A | 12/1981 | Martin |
| 4,308,250 A | 12/1981 | Griffin |

(Continued)

FOREIGN PATENT DOCUMENTS

| | | |
|---|---|---|
| AU | 601478 B2 | 9/1990 |
| CA | 681997 | 3/1964 |

(Continued)

OTHER PUBLICATIONS

J.H. Briston, "Plastic Films", 1974, pp. 96-97.

(Continued)

*Primary Examiner* — Lezah Roberts
(74) *Attorney, Agent, or Firm* — Parker D. McCrary; Kelly L. McDow

(57) ABSTRACT

A tooth whitening product is provided. The tooth whitening product has a backing layer and a tooth whitening composition. The tooth whitening composition includes first and second water soluble polymers, water, and a tooth whitening agent, wherein the first water soluble polymer is polyethelene oxide and the second water soluble polymer is polyvinyl alcohol.

15 Claims, 3 Drawing Sheets

(56) References Cited

U.S. PATENT DOCUMENTS

| | | |
|---|---|---|
| 4,324,547 A | 4/1982 | Arcan et al. |
| 4,325,855 A | 4/1982 | Dickmann |
| 4,331,576 A | 5/1982 | Colon |
| 4,335,731 A | 6/1982 | Bora |
| 4,363,843 A | 12/1982 | Crofts |
| 4,373,036 A | 2/1983 | Chang |
| 4,376,628 A | 3/1983 | Aardse |
| 4,428,373 A | 1/1984 | Seid |
| 4,431,631 A | 2/1984 | Clipper |
| 4,438,258 A | 3/1984 | Graham |
| 4,442,258 A | 4/1984 | Sunakawa |
| 4,460,562 A | 7/1984 | Keith |
| 4,503,070 A | 3/1985 | Eby, III |
| 4,513,243 A | 4/1985 | Novak |
| 4,515,162 A | 5/1985 | Yamamoto |
| 4,517,173 A | 5/1985 | Kizawa |
| 4,518,721 A | 5/1985 | Dhabhar |
| 4,522,593 A | 6/1985 | Fischer |
| 4,522,805 A | 6/1985 | Gordon |
| 4,522,806 A | 6/1985 | Muhlemann |
| 4,528,180 A | 7/1985 | Schaeffer |
| 4,529,748 A | 7/1985 | Wienecke |
| 4,532,063 A | 7/1985 | Gueldenzopf |
| 4,537,778 A | 8/1985 | Clipper |
| 4,544,354 A | 10/1985 | Gores |
| 4,554,154 A | 11/1985 | White |
| 4,557,692 A | 12/1985 | Chorbajian |
| 4,560,351 A | 12/1985 | Osborne |
| 4,568,536 A | 2/1986 | Kronenthal |
| 4,592,487 A | 6/1986 | Simon |
| 4,592,488 A | 6/1986 | Simon |
| 4,592,726 A | 6/1986 | Brilliant |
| 4,593,053 A | 6/1986 | Jevne |
| 4,623,394 A | 11/1986 | Nakamura |
| 4,640,685 A | 2/1987 | Croll |
| 4,650,665 A | 3/1987 | Kronenthal |
| 4,661,070 A | 4/1987 | Friedman |
| 4,687,663 A | 8/1987 | Schaeffer |
| 4,690,996 A | 9/1987 | Shih |
| 4,695,465 A | 9/1987 | Kazuo |
| 4,696,757 A | 9/1987 | Blank |
| 4,712,460 A | 12/1987 | Allen |
| 4,713,239 A | 12/1987 | Babaian |
| 4,713,243 A | 12/1987 | Schiraldi |
| 4,722,761 A | 2/1988 | Cartmell |
| 4,728,291 A | 3/1988 | Golub |
| 4,741,700 A | 5/1988 | Barabe |
| 4,741,941 A | 5/1988 | Englebert et al. |
| 4,755,385 A | 7/1988 | Etienne |
| 4,755,386 A | 7/1988 | Hsiao |
| 4,765,983 A | 8/1988 | Takayanagi |
| 4,770,634 A | 9/1988 | Pellico |
| 4,772,470 A | 9/1988 | Inoue |
| 4,777,046 A | 10/1988 | Iwakura |
| 4,786,253 A | 11/1988 | Morals |
| 4,788,052 A | 11/1988 | Ng |
| 4,797,283 A | 1/1989 | Allen |
| 4,799,888 A | 1/1989 | Golub |
| 4,812,308 A | 3/1989 | Winston |
| 4,828,113 A | 5/1989 | Friedland et al. |
| 4,837,008 A | 6/1989 | Rudy |
| 4,839,156 A | 6/1989 | Ng |
| 4,839,157 A | 6/1989 | Mei-King Ng |
| 4,849,213 A | 7/1989 | Schaeffer |
| 4,849,246 A | 7/1989 | Schmidt |
| 4,860,754 A | 8/1989 | Sharik |
| RE33,093 E | 10/1989 | Schiraldi et al. |
| 4,876,092 A | 10/1989 | Mizobuchi |
| 4,891,400 A | 1/1990 | Schwabe |
| 4,895,517 A | 1/1990 | Fischer |
| 4,895,721 A | 1/1990 | Drucker |
| 4,900,253 A | 1/1990 | Landis |
| 4,900,552 A | 2/1990 | Sanvordeker |
| 4,900,554 A | 2/1990 | Yanagibashi |
| 4,902,227 A | 2/1990 | Smith |
| 4,910,247 A | 3/1990 | Haldar |
| 4,915,950 A | 4/1990 | Miranda |
| 4,919,615 A | 4/1990 | Croll |
| 4,925,670 A | 5/1990 | Schmidt |
| 4,927,634 A | 5/1990 | Sorrentino |
| 4,927,636 A | 5/1990 | Hijiya |
| 4,931,282 A | 6/1990 | Asmus |
| 4,949,580 A | 8/1990 | Browing |
| 4,950,479 A | 8/1990 | Hill |
| 4,968,251 A | 11/1990 | Darnell |
| 4,971,782 A | 11/1990 | Rudy |
| 4,972,946 A | 11/1990 | Whittaker |
| 4,980,152 A | 12/1990 | Frazier |
| 4,983,379 A | 1/1991 | Schaeffer |
| 4,983,381 A | 1/1991 | Zaragoza |
| 4,988,500 A | 1/1991 | Hunter |
| 4,990,089 A | 2/1991 | Munro |
| 5,001,170 A | 3/1991 | Keegan |
| 5,008,106 A | 4/1991 | Merianos |
| 5,009,881 A | 4/1991 | Hill |
| 5,015,180 A | 5/1991 | Randklev |
| 5,024,701 A | 6/1991 | Desmarais |
| 5,032,387 A | 7/1991 | Hill |
| 5,047,244 A | 9/1991 | Sanvordeker |
| 5,059,120 A | 10/1991 | Lee |
| 5,059,417 A | 10/1991 | Williams |
| 5,064,717 A | 11/1991 | Suzuki |
| 5,076,791 A | 12/1991 | Madray, Jr. |
| 5,084,268 A | 1/1992 | Thaler |
| 5,098,303 A | 3/1992 | Fischer |
| 5,122,365 A | 6/1992 | Murayama |
| 5,158,825 A | 10/1992 | Altwirth |
| 5,160,737 A | 11/1992 | Friedman |
| 5,165,424 A | 11/1992 | Silverman |
| 5,166,233 A | 11/1992 | Kuroya et al. |
| 5,171,564 A | 12/1992 | Nathoo |
| 5,186,938 A | 2/1993 | Sablotsky |
| RE34,196 E | 3/1993 | Munroe |
| 5,192,802 A | 3/1993 | Rencher |
| 5,211,559 A | 5/1993 | Hart et al. |
| 5,229,164 A | 7/1993 | Pins |
| 5,234,342 A | 8/1993 | Fischer |
| 5,240,415 A | 8/1993 | Haynie |
| 5,246,371 A | 9/1993 | Fischer |
| 5,252,334 A | 10/1993 | Chiang |
| 5,256,402 A | 10/1993 | Prencipe |
| 5,271,940 A | 12/1993 | Cleary |
| 5,288,231 A | 2/1994 | Kuehn et al. |
| 5,288,498 A | 2/1994 | Stanley |
| 5,290,566 A | 3/1994 | Schow |
| 5,310,563 A | 5/1994 | Curtis et al. |
| 5,314,915 A | 5/1994 | Rencher |
| 5,320,831 A | 6/1994 | Majeti et al. |
| 5,326,685 A | 7/1994 | Gaglio et al. |
| 5,330,746 A | 7/1994 | Friedman |
| 5,332,576 A | 7/1994 | Mantelle |
| 5,340,314 A | 8/1994 | Tarvis |
| 5,340,581 A | 8/1994 | Tseng et al. |
| 5,344,702 A | 9/1994 | Haubs |
| 5,354,551 A | 10/1994 | Schmidt |
| 5,356,291 A | 10/1994 | Darnell |
| 5,364,267 A | 11/1994 | Fischer |
| 5,376,006 A | 12/1994 | Fischer |
| 5,380,198 A | 1/1995 | Suhonen |
| 5,387,103 A | 2/1995 | Fischer |
| 5,393,528 A | 2/1995 | Staab |
| 5,401,495 A | 3/1995 | Murayama |
| 5,401,528 A | 3/1995 | Schmidt |
| 5,409,631 A | 4/1995 | Fischer |
| 5,409,703 A | 4/1995 | McAnalley |
| 5,420,197 A | 5/1995 | Lorenz |
| 5,425,641 A | 6/1995 | Fischer |
| 5,425,953 A | 6/1995 | Sintov |
| 5,427,770 A | 6/1995 | Viccaro |
| 5,438,076 A | 8/1995 | Friedman et al. |
| 5,455,043 A | 10/1995 | Fischel-Ghodsian |
| 5,456,745 A | 10/1995 | Roreger |
| 5,462,749 A | 10/1995 | Rencher |
| 5,464,348 A | 11/1995 | Fischer |

(56) References Cited

U.S. PATENT DOCUMENTS

| | | |
|---|---|---|
| 5,472,704 A | 12/1995 | Santus |
| 5,474,780 A | 12/1995 | Chang |
| 5,505,933 A | 4/1996 | Norfleet |
| 5,509,800 A | 4/1996 | Cunningham |
| 5,522,726 A | 6/1996 | Hodosh |
| 5,529,782 A | 6/1996 | Staab |
| 5,534,562 A | 7/1996 | Fischer |
| 5,560,379 A | 10/1996 | Pieczenik |
| 5,565,190 A | 10/1996 | Santalucia |
| 5,575,654 A | 11/1996 | Pontenot |
| 5,575,655 A | 11/1996 | Darnell |
| 5,579,523 A | 11/1996 | Tanaka |
| 5,593,684 A | 1/1997 | Baker |
| 5,599,553 A | 2/1997 | Chung |
| 5,603,701 A | 2/1997 | Fischer |
| 5,611,687 A | 3/1997 | Wagner |
| 5,613,942 A | 3/1997 | Lucast |
| 5,616,027 A | 4/1997 | Jacobs et al. |
| 5,618,273 A | 4/1997 | Fischer |
| 5,620,322 A | 4/1997 | Lococo |
| 5,626,866 A | 5/1997 | Ebert et al. |
| 5,629,003 A | 5/1997 | Horstmann |
| 5,631,000 A | 5/1997 | Pellico |
| 5,631,055 A | 5/1997 | Vines et al. |
| 5,635,162 A | 6/1997 | Fischer |
| 5,639,445 A | 6/1997 | Curtis et al. |
| 5,648,064 A | 7/1997 | Gaffar et al. |
| 5,660,178 A | 8/1997 | Kantner |
| 5,662,758 A | 9/1997 | Hamilton |
| 5,678,273 A | 10/1997 | Porcelli |
| 5,685,712 A | 11/1997 | Fischer |
| 5,686,094 A | 11/1997 | Acharya |
| 5,692,900 A | 12/1997 | Fischer |
| 5,700,148 A | 12/1997 | Fischer |
| 5,700,478 A | 12/1997 | Biegajski |
| 5,707,235 A | 1/1998 | Knutson |
| 5,707,736 A | 1/1998 | Levy et al. |
| 5,708,052 A | 1/1998 | Fischer |
| 5,713,738 A | 2/1998 | Yarborough |
| 5,722,833 A | 3/1998 | Fischer |
| 5,723,132 A | 3/1998 | Tseng et al. |
| 5,725,843 A | 3/1998 | Fischer |
| 5,746,598 A | 5/1998 | Fischer |
| 5,759,037 A | 6/1998 | Fischer |
| 5,759,038 A | 6/1998 | Fischer |
| 5,766,011 A | 6/1998 | Sibner |
| 5,770,105 A | 6/1998 | Fischer |
| 5,770,182 A | 6/1998 | Fischer |
| 5,770,219 A | 6/1998 | Chiang |
| 5,780,045 A | 7/1998 | McQuinn |
| 5,785,955 A | 7/1998 | Fischer |
| 5,788,579 A | 8/1998 | Cherry et al. |
| 5,800,832 A | 9/1998 | Tapolsky |
| 5,816,804 A | 10/1998 | Fischer |
| 5,819,765 A | 10/1998 | Mittiga |
| 5,827,525 A | 10/1998 | Liao et al. |
| 5,827,591 A | 10/1998 | Blok |
| 5,846,058 A | 12/1998 | Fischer |
| 5,851,512 A | 12/1998 | Fischer |
| 5,851,551 A | 12/1998 | Tseng |
| 5,855,870 A | 1/1999 | Fischer |
| 5,856,282 A | 1/1999 | Hughes |
| 5,858,332 A | 1/1999 | Jensen |
| 5,860,809 A | 1/1999 | Meehan |
| 5,863,202 A | 1/1999 | Fontenot |
| 5,879,591 A | 3/1999 | Nagoh et al. |
| 5,879,691 A | 3/1999 | Sagel et al. |
| 5,888,480 A | 3/1999 | Homola et al. |
| 5,891,453 A | 4/1999 | Sagel |
| 5,894,017 A | 4/1999 | Sagel |
| 5,902,568 A | 5/1999 | Ryles |
| 5,922,307 A | 7/1999 | Montgomery |
| 5,948,430 A | 9/1999 | Zerbe |
| 5,950,830 A | 9/1999 | Trigger |
| 5,953,885 A | 9/1999 | Berman |
| 5,968,500 A | 10/1999 | Robinson |
| 5,968,633 A | 10/1999 | Hamilton |
| 5,908,868 A | 11/1999 | Homola et al. |
| 5,980,249 A | 11/1999 | Fontenot |
| 5,980,932 A | 11/1999 | Chiang |
| 5,981,499 A | 11/1999 | Hau |
| 5,985,249 A | 11/1999 | Fischer |
| 5,989,526 A | 11/1999 | Dorrit |
| 5,989,569 A | 11/1999 | Dirksing |
| 6,008,171 A | 12/1999 | Hughes |
| 6,019,962 A | 2/2000 | Rabe |
| 6,024,891 A | 2/2000 | Hughes |
| 6,030,222 A | 2/2000 | Tarver |
| 6,036,943 A | 3/2000 | Fischer |
| 6,045,811 A | 4/2000 | Dirksing et al. |
| 6,071,503 A | 6/2000 | Drechsler |
| 6,072,100 A | 6/2000 | Mooney |
| 6,074,654 A | 6/2000 | Drechsler |
| 6,077,502 A | 6/2000 | Witt |
| 6,083,421 A | 7/2000 | Huang |
| 6,086,855 A | 7/2000 | Fischer |
| 6,090,401 A | 7/2000 | Gowan, Jr. |
| 6,094,889 A | 8/2000 | VanLoon |
| 6,096,328 A | 8/2000 | Sagel et al. |
| 6,106,293 A | 8/2000 | Wiesel |
| 6,123,950 A | 9/2000 | Hughes |
| 6,126,443 A | 10/2000 | Burgio |
| 6,129,929 A | 10/2000 | Wick |
| 6,132,702 A | 10/2000 | Witt |
| 6,136,297 A | 10/2000 | Sagel et al. |
| 6,139,820 A | 10/2000 | Fischer |
| 6,139,823 A | 10/2000 | Drechsler |
| 6,142,780 A | 11/2000 | Burgio |
| 6,146,655 A | 11/2000 | Ruben |
| 6,149,895 A | 11/2000 | Kutsch |
| 6,155,825 A | 12/2000 | Fischer |
| 6,155,832 A | 12/2000 | Wiesel |
| 6,159,498 A | 12/2000 | Tapolsky |
| 6,177,096 B1 | 1/2001 | Zerbe |
| 6,182,420 B1 | 2/2001 | Berman |
| 6,183,251 B1 | 2/2001 | Fischer |
| 6,197,331 B1 | 3/2001 | Lerner |
| 6,210,699 B1 | 4/2001 | Acharya |
| 6,211,296 B1 | 4/2001 | Frate |
| 6,217,335 B1 | 4/2001 | Rittan |
| 6,231,957 B1 | 5/2001 | Zerbe |
| 6,234,793 B1 | 5/2001 | Fischer |
| 6,248,363 B1 | 6/2001 | Patel |
| 6,261,679 B1 | 7/2001 | Chen et al. |
| 6,274,122 B1 | 8/2001 | McLaughlin |
| 6,277,458 B1 | 8/2001 | Dirksing |
| 6,284,264 B1 | 9/2001 | Zerbe |
| 6,287,120 B1 | 9/2001 | Wiesel |
| 6,306,206 B1 | 10/2001 | Fischer |
| 6,306,370 B1 | 10/2001 | Jensen |
| 6,309,625 B1 | 10/2001 | Jensen |
| 6,312,671 B1 | 11/2001 | Jensen |
| 6,322,360 B1 | 11/2001 | Burgio |
| 6,331,292 B1 | 12/2001 | Montgomery |
| 6,337,086 B1 | 1/2002 | Kanios |
| 6,340,466 B1 | 1/2002 | Drechsler |
| 6,343,932 B1 | 2/2002 | Wiesel |
| 6,368,576 B1 | 4/2002 | Jensen |
| 6,375,963 B1 | 4/2002 | Repka |
| 6,379,155 B1 | 4/2002 | Rittano |
| 6,379,654 B1 | 4/2002 | Gebreselassie |
| 6,391,283 B1 | 5/2002 | Jensen |
| 6,402,514 B1 | 5/2002 | Fischer |
| 6,400,801 B1 | 6/2002 | Fischer |
| 6,406,683 B1 | 6/2002 | Drechsler |
| 6,419,903 B1 | 7/2002 | Xu |
| 6,419,906 B1 | 7/2002 | Xu et al. |
| 6,461,158 B1 | 10/2002 | Sagel |
| 6,468,079 B1 | 10/2002 | Fischer |
| 6,488,914 B2 | 12/2002 | Montgomery |
| 6,500,004 B2 | 12/2002 | Jensen |
| 6,500,408 B2 | 12/2002 | Chen |
| 6,503,486 B2 | 1/2003 | Xu |
| 6,514,483 B2 | 2/2003 | Xu |

(56) References Cited

U.S. PATENT DOCUMENTS

| | | |
|---|---|---|
| 6,517,350 B2 | 2/2003 | Diasti |
| 6,537,565 B2 | 3/2003 | Swanbom |
| 6,585,997 B2 | 3/2003 | Moro |
| 6,551,579 B2 | 4/2003 | Sagel |
| 6,552,024 B1 | 4/2003 | Chen |
| 6,576,712 B2 | 6/2003 | Feldstein |
| 6,582,708 B1 | 6/2003 | Sagel |
| 6,589,512 B1 | 7/2003 | Yue |
| 6,592,887 B2 | 7/2003 | Zerbe |
| 6,596,298 B2 | 7/2003 | Leung |
| 6,625,839 B2 | 9/2003 | Fischer |
| 6,635,272 B2 | 10/2003 | Leaderman |
| 6,649,147 B1 | 11/2003 | Ye et al. |
| 6,652,282 B2 | 11/2003 | Jensen |
| 6,669,930 B1 | 12/2003 | Hoic |
| 6,682,721 B2 | 1/2004 | Kim et al. |
| 6,682,756 B1 | 1/2004 | Horstmann |
| 6,685,921 B2 | 2/2004 | Lawlor |
| 6,689,344 B2 | 2/2004 | Chang |
| 6,692,727 B1 | 2/2004 | Yue et al. |
| 6,703,040 B2 | 3/2004 | Katsarava |
| 6,709,671 B2 | 3/2004 | Zerbe |
| 6,719,995 B2 | 4/2004 | Rajaiah |
| 6,729,879 B2 | 5/2004 | Allred |
| 6,730,316 B2 | 5/2004 | Chen |
| 6,737,080 B1 | 5/2004 | Schumann |
| 6,756,417 B2 | 6/2004 | Allred |
| 6,814,794 B2 | 11/2004 | Allred |
| 6,860,736 B2 | 3/2005 | Allred |
| 6,884,426 B2 | 4/2005 | Sagel |
| 6,916,463 B2 | 7/2005 | Lee et al. |
| 6,946,142 B2 | 9/2005 | Chang |
| 6,949,240 B2 | 9/2005 | Sagel et al. |
| 6,981,874 B2 | 1/2006 | Allred |
| 6,994,546 B2 | 2/2006 | Fischer |
| 6,997,706 B2 | 2/2006 | Jessop |
| 6,997,708 B2 | 2/2006 | Allred |
| 7,011,523 B2 | 3/2006 | Allred |
| 7,018,622 B2 | 3/2006 | Goodhart et al. |
| 7,025,983 B2 | 4/2006 | Leung |
| 7,040,893 B2 | 5/2006 | Fischer |
| 7,040,897 B2 | 5/2006 | Fischer |
| 7,048,543 B2 | 5/2006 | Allred |
| 7,052,275 B2 | 5/2006 | Allred |
| 7,056,118 B2 | 6/2006 | Allred |
| 7,059,857 B2 | 6/2006 | Allred |
| 7,059,858 B2 | 6/2006 | McLean |
| 7,074,042 B2 | 7/2006 | Allred |
| 7,094,393 B2 | 8/2006 | Montgomery |
| 7,097,449 B2 | 8/2006 | Jessop |
| 7,121,828 B2 | 10/2006 | Fischer |
| 7,122,199 B2 | 10/2006 | Sagel |
| 7,128,899 B2 | 10/2006 | Chen |
| 7,144,250 B2 | 12/2006 | Fischer |
| 7,168,951 B2 | 1/2007 | Fischer |
| 7,172,423 B2 | 2/2007 | Allred |
| 7,192,276 B2 | 3/2007 | Fischer |
| 7,192,280 B2 | 3/2007 | Allred |
| 7,198,623 B2 | 4/2007 | Fischer |
| 2001/0009755 A1 | 7/2001 | Fischer |
| 2001/0021828 A1 | 9/2001 | Fischer |
| 2001/0024657 A1 | 9/2001 | Lerner |
| 2002/0006387 A1 | 1/2002 | Sagel et al. |
| 2002/0126785 A1 | 1/2002 | Sagel et al. |
| 2002/0018754 A1 | 2/2002 | Sagel |
| 2002/0081556 A1 | 6/2002 | Tseng |
| 2002/0127190 A1 | 9/2002 | Zerbe |
| 2002/0127254 A1 | 9/2002 | Fotinos |
| 2002/0131990 A1 | 9/2002 | Barkalow |
| 2002/0141950 A1 | 10/2002 | Chen |
| 2002/0146666 A1 | 10/2002 | Sagel et al. |
| 2002/0187111 A1 | 12/2002 | Xu et al. |
| 2002/0187181 A1 | 12/2002 | Godbey |
| 2003/0035841 A1 | 2/2003 | Dzija |
| 2003/0049209 A1 | 3/2003 | Tseng |
| 2003/0054039 A1 | 3/2003 | Zyck |
| 2003/0082115 A1 | 5/2003 | Allred |
| 2003/0099690 A1 | 5/2003 | Awamura |
| 2003/0145863 A1 | 8/2003 | Allred |
| 2003/0147258 A1 | 8/2003 | Fischer |
| 2003/0148242 A1 | 8/2003 | Fischer |
| 2003/0152528 A1 | 8/2003 | Singh |
| 2003/0156980 A1 | 8/2003 | Fischer |
| 2003/0170308 A1 | 9/2003 | Cleary |
| 2003/0194382 A1 | 10/2003 | Chang |
| 2003/0199605 A1 | 10/2003 | Fischer |
| 2003/0211056 A1 | 11/2003 | Sagel |
| 2003/0212372 A1 | 11/2003 | Fischer |
| 2003/0215766 A1 | 11/2003 | Fischer |
| 2003/0219389 A1 | 11/2003 | Sagel |
| 2003/0219390 A1 | 11/2003 | Santarpia |
| 2003/0228264 A1 | 12/2003 | Perna |
| 2004/0005277 A1 | 1/2004 | Willison |
| 2004/0022755 A1 | 2/2004 | Kamar |
| 2004/0043134 A1 | 3/2004 | Corriveau |
| 2004/0062724 A1 | 4/2004 | Moro |
| 2004/0086468 A1 | 5/2004 | Prosise |
| 2004/0091432 A1 | 5/2004 | Dulin |
| 2004/0096569 A1 | 5/2004 | Barkalow |
| 2004/0101496 A1 | 5/2004 | Chen |
| 2004/0105834 A1 | 6/2004 | Singh |
| 2004/0120903 A1 | 6/2004 | Sagel |
| 2004/0122377 A1 | 6/2004 | Fischer |
| 2004/0136927 A1 | 7/2004 | Kim |
| 2004/0209229 A1 | 10/2004 | Jensen |
| 2004/0214130 A1 | 10/2004 | Fischer |
| 2004/0214131 A1 | 10/2004 | Fischer |
| 2004/0214140 A1 | 10/2004 | Fischer |
| 2004/0219190 A1 | 11/2004 | Kosti |
| 2004/0223933 A1 | 11/2004 | Chen |
| 2004/0249016 A1 | 12/2004 | Allread |
| 2004/0258723 A1 | 12/2004 | Singh |
| 2005/0016884 A1 | 1/2005 | Stout |
| 2005/0019275 A1 | 1/2005 | Sagel |
| 2005/0019277 A1 | 1/2005 | Sagel et al. |
| 2005/0031554 A1 | 2/2005 | Kim |
| 2005/0031675 A1 | 2/2005 | Spence Leung |
| 2005/0048102 A1 | 3/2005 | Tapolsky |
| 2005/0064371 A1 | 3/2005 | Soukos |
| 2005/0069837 A1 | 3/2005 | Lewis |
| 2005/0100515 A1 | 5/2005 | Sagel |
| 2005/0130096 A1 | 6/2005 | Stout |
| 2005/0136373 A1 | 6/2005 | Fischer |
| 2005/0137109 A1 | 6/2005 | Quan |
| 2005/0137110 A1 | 6/2005 | Scott |
| 2005/0147658 A1 | 7/2005 | Tapolsky |
| 2005/0163820 A1 | 7/2005 | Fischer |
| 2005/0186150 A1 | 8/2005 | Allred |
| 2005/0196726 A1 | 8/2005 | Fischer |
| 2005/0208110 A1 | 9/2005 | Singh |
| 2005/0215727 A1 | 9/2005 | Feldstein |
| 2005/0238591 A1 | 10/2005 | Sagel |
| 2005/0249677 A1 | 11/2005 | Malcmacher |
| 2005/0249680 A1 | 11/2005 | Goodhart |
| 2005/0249780 A1 | 11/2005 | Goodhart |
| 2005/0260544 A1 | 11/2005 | Jones et al. |
| 2005/0287086 A1 | 12/2005 | Sagel |
| 2006/0263307 A1 | 11/2006 | Robillard |
| 2007/0003495 A1 | 1/2007 | Sagel |
| 2007/0086891 A1 | 4/2007 | Sagel |
| 2007/0086961 A1 | 4/2007 | Sagel |
| 2007/0218015 A1 | 9/2007 | Hardy |
| 2007/0253990 A1 | 11/2007 | Sagel |
| 2007/0259011 A1 | 11/2007 | Sagel |
| 2007/0269388 A1 | 11/2007 | Sagel |
| 2007/0269471 A1 | 11/2007 | Sagel |
| 2007/0269491 A1 | 11/2007 | Sagel |
| 2007/0269520 A1 | 11/2007 | Sagel |
| 2007/0269521 A1 | 11/2007 | Sagel |
| 2007/0275023 A1 | 11/2007 | Sagel |
| 2007/0275041 A1 | 11/2007 | Sagel |
| 2007/0297994 A1 | 12/2007 | Sagel |
| 2007/0298088 A1 | 12/2007 | Sagel |
| 2008/0011636 A1 | 1/2008 | St. John |

(56) References Cited

U.S. PATENT DOCUMENTS

| | | |
|---|---|---|
| 2008/0025923 A1 | 1/2008 | Sagel |
| 2008/0025924 A1 | 1/2008 | Sagel |
| 2008/0025927 A1 | 1/2008 | Sagel |
| 2008/0025928 A1 | 1/2008 | Sagel |
| 2008/0026021 A1 | 1/2008 | Sagel |
| 2008/0031910 A1 | 2/2008 | Sagel |
| 2008/0038211 A1 | 2/2008 | Sagel |
| 2008/0226567 A1 | 9/2008 | Sagel |
| 2009/0181071 A1 | 1/2009 | St. John |
| 2009/0092564 A1 | 4/2009 | Sagel et al. |
| 2011/0014252 A1 | 1/2011 | Sagel et al. |
| 2012/0189680 A1 | 7/2012 | Sagel et al. |

FOREIGN PATENT DOCUMENTS

| | | |
|---|---|---|
| CA | 1209761 | 8/1986 |
| CA | 2078960 | 10/1993 |
| CA | 2095445 | 7/1995 |
| CA | 2000040 | 10/1995 |
| CA | 2162536 | 5/1996 |
| CA | 2162812 | 5/1996 |
| CA | 2162885 | 5/1996 |
| DE | 871818 | 3/1953 |
| DE | 1104116 | 4/1961 |
| DE | 2330869 | 1/1975 |
| DE | 29701552 | 5/1997 |
| EP | 00636604 | 11/1982 |
| EP | 0 063 604 | 3/1984 |
| EP | 0 109 269 A1 | 5/1984 |
| EP | 0 109 269 B1 | 7/1986 |
| EP | 0 200 508 | 12/1986 |
| EP | 0 219 762 | 4/1987 |
| EP | 0 232 006 A2 | 8/1987 |
| EP | 0 252 459 | 1/1988 |
| EP | 0 273 069 A1 | 7/1988 |
| EP | 0 288 420 A1 | 10/1988 |
| EP | 0 328 317 A1 | 8/1989 |
| EP | 0 381 194 | 8/1990 |
| EP | 0 273 069 B1 | 10/1992 |
| EP | 0 511 782 | 11/1992 |
| EP | 0 539 751 A1 | 5/1993 |
| EP | 0 569 797 A2 | 11/1993 |
| EP | 0 599 435 A1 | 6/1994 |
| EP | 0 636 378 A1 | 2/1995 |
| EP | 0 637 446 A1 | 2/1995 |
| EP | 0 743 059 | 11/1996 |
| EP | 0 763 358 | 3/1997 |
| EP | 0 854 112 | 7/1998 |
| EP | 0 864 315 | 9/1998 |
| EP | 0 899 208 | 3/1999 |
| EP | 1 153 594 A2 | 11/2001 |
| EP | 0250187 | 9/2003 |
| FR | 2637 175 A1 | 4/1990 |
| FR | 2701397 | 2/1998 |
| GB | 1142325 | 2/1969 |
| GB | 1240411 | 7/1971 |
| GB | 2108841 | 5/1983 |
| GB | 2 115 431 A | 9/1983 |
| GB | 2 159 052 A | 11/1985 |
| IE | 42604 | 9/1980 |
| JP | 57-028102 | 2/1982 |
| JP | 58-213709 A | 12/1983 |
| JP | 60005159 A | 1/1985 |
| JP | 60005160 A | 1/1985 |
| JP | 61280423 | 12/1986 |
| JP | 62-142113 A | 6/1987 |
| JP | 62-225417 A | 11/1987 |
| JP | 630005756 | 1/1988 |
| JP | 63-054318 A | 3/1988 |
| JP | 64-040423 | 2/1989 |
| JP | 1-279838 | 11/1989 |
| JP | 1279838 | 11/1989 |
| JP | 03-264522 A | 3/1990 |
| JP | 02-202814 A | 8/1990 |
| JP | 2250826 | 10/1990 |
| JP | 3198754 | 8/1991 |
| JP | 3-264522 | 11/1991 |
| JP | 3-264523 | 11/1991 |
| JP | 5-124954 | 5/1993 |
| JP | 06-321774 A | 5/1993 |
| JP | 5220203 A2 | 8/1993 |
| JP | 5-236885 | 9/1993 |
| JP | 7-100186 | 4/1995 |
| JP | 7126133 | 5/1995 |
| JP | 8183732 | 7/1996 |
| JP | 08325128 A2 | 12/1996 |
| JP | 10-017448 A | 1/1998 |
| JP | 10226639 | 8/1998 |
| JP | 1222420 | 8/1999 |
| JP | 2003137756 A2 | 5/2003 |
| KR | 20030059552 | 7/2009 |
| RU | 2075965 C1 | 9/1994 |
| WO | WO 88/06879 | 9/1988 |
| WO | WO 89/10740 | 11/1989 |
| WO | WO 90/15592 | 12/1990 |
| WO | WO 91/03236 | 3/1991 |
| WO | WO 91/06270 | 5/1991 |
| WO | WO 91/06289 | 5/1991 |
| WO | WO 91/16041 | 10/1991 |
| WO | WO 92/10161 | 6/1992 |
| WO | WO 93/01790 | 2/1993 |
| WO | WO 95/05416 | 2/1995 |
| WO | WO 95/09603 | 4/1995 |
| WO | WO 95/15158 | 6/1995 |
| WO | WO 95/17158 | 6/1995 |
| WO | WO 95/24872 | 9/1995 |
| WO | WO 96/25910 | 8/1996 |
| WO | WO 97/17059 | 5/1997 |
| WO | WO 97/25968 | 7/1997 |
| WO | WO 98/17263 | 4/1998 |
| WO | WO 98/55044 | 12/1998 |
| WO | WO 98/55079 | 12/1998 |
| WO | WO 99/20237 | 4/1999 |
| WO | WO 99/27895 | 6/1999 |
| WO | WO 99/62472 | 12/1999 |
| WO | WO 99/66870 | 12/1999 |
| WO | WO 00/42992 | 7/2000 |
| WO | WO 00/044845 | 8/2000 |
| WO | WO 00/54699 | 9/2000 |
| WO | WO 01/01942 | 1/2001 |
| WO | WO 01/001958 | 1/2001 |
| WO | WO 01/01958 A1 | 1/2001 |
| WO | WO 01/030263 | 5/2001 |
| WO | WO 01/134107 | 5/2001 |
| WO | WO 01/68045 | 9/2001 |
| WO | WO 01/68045 A1 | 9/2001 |
| WO | WO 02/00182 | 1/2002 |
| WO | WO 02/02085 A2 | 1/2002 |
| WO | WO 02/04570 | 1/2002 |
| WO | WO 02/07636 | 1/2002 |
| WO | WO 02/26196 A1 | 4/2002 |
| WO | WO 02/40068 | 5/2002 |
| WO | WO 02/02085 A3 | 6/2002 |
| WO | WO 02/43657 A2 | 6/2002 |
| WO | WO 02/060779 | 8/2002 |
| WO | WO 02/087645 | 11/2002 |
| WO | WO 02/092049 A2 | 11/2002 |
| WO | WO 03/011259 A1 | 2/2003 |
| WO | WO 03/043659 A1 | 5/2003 |
| WO | WO 03/072075 A | 9/2003 |
| WO | WO 03/086337 | 10/2003 |
| WO | WO 03/101360 A | 12/2003 |
| WO | WO 2004/071323 | 8/2004 |
| WO | WO 2004/103201 | 12/2004 |
| WO | WO 2005/027768 | 3/2005 |
| WO | WO 2005/074894 | 8/2005 |
| WO | WO 06/124983 | 11/2006 |

OTHER PUBLICATIONS

G. McLaughlin, et al., "Materials" and "Clinical Techniques", *Color Atlas of Tooth Whitening*, 1991, pp. 35-38 & 45-50, Ishiyaku EuroAmerica, Inc.

(56) References Cited

OTHER PUBLICATIONS

S.M. Newman, et al., "Tray-Forming Technique for Dentist-Supervised Home Bleaching", *Quintessence International*, 1995, pp. 447-453, vol. 26, No. 7.
3M Dental Products 2000 Product Catalog, 32 pages.
Besner, E., et al., Practical Endodontics, 1994, pp. 7-15, 178-180; Mosby-Year Book, Inc.
Howard Frysh, BDS, DDS., "Chemistry of Bleaching", *Complete Dental Bleaching*, 1995, pp. 25-32 & 90-97, Quintessence Publishing Co, Inc.
V.B. Haywood, et al., "Nightguard Vital Bleaching", *Quintessence International*, 1989, vol. 20, No. 3, pp. 173-176, 19$^{th}$ International Meeting on Dental Implants and Transplants, Bologna, Italy.
V.B. Haywood, "History, Safety, and Effectiveness of Current Bleaching Techniques and Applications of the Nightguard Vital Bleaching Technique", *Quintessence International*, 1992, vol. 23, No. 7, pp. 471-488.
V.B. Haywood, "Nightguard Vital Bleaching", *Dentistry Today*, 1997, pp. 88-91.
"Tooth Bleaching, Home-Use Products", *Clinical Research Associates Newsletter*, 1989, vol. 3, Issue 12.
Ralph H. Leonard Jr., et al, "Risk factors for developing tooth sensitivity and gingival irritation associated with nightguard vital bleaching", *Esthetic Dentistry*, 1997, vol. 28,No. 8, pp. 527-534.
Van B. Haywood, et al, "Nightguard vital bleaching: how safe is it?", *Esthetic Dentistry*, 1991, vol. 22, No. 7, pp. 515-523.
Van B. Haywood, "Bleaching of vital and not vital teeth", *Periodontology and Restorative Dentistry*, 1992, pp. 142-149.
Van B. Haywood, "Nightquard vital bleaching, a history and products update: Part 1", *Esthestic Dentistry Update*, 1991, vol. 2, No. 4, pp. 63-66.
Van B. Haywood, "Nightguard vital bleaching, a history and products update: Part 2", *Esthestic Dentistry Update*, 1991, vol. 2, No. 5, pp. 82-85.
Claudia Paula Drew, "Teeth Bleaching . . . a Vital technique for you to know", 1988, Sep./Oct., pp. 23-25.
Van Benjamin Haywood, "Overview and Status of Mouthguard Bleaching" *Journal of Esthetic Dentistry*, 1991, vol. 3, No. 5, pp. 157-161.
Van B. Haywood, "Nightguard vital bleaching: current information and research", *Esthetic Dentistry Update*, 1990, vol. 1, No. 2, pp. 20-25.
Carolyn F. G. Wilson, et al, "Color change following vital bleaching of tetracycline-stained teeth" *Pediatric Dentistry*, 1985, vol. 7, No. 3, pp. 205-208.
"Tooth Bleaching, Home-Use Products", *Clinical Research Associates Newsletter*, Jul. 1989, pp. 1-4.
Sue Ellen Richardson, "Home bleaching: effectiveness, history, technique, bleaches, cost and safety" *The Journal of the Greater Houston Dental Society*, 1989, pp. 22-26.
Van B. Haywood, "The food and drug administration and its influence on home bleaching", *ADA*, 1993, pp. 12-18.
Van B. Haywood, "Efficacy of foam liner in 10% carbamide peroxide bleaching technique", *Esthetic Dentistry*, 1993, vol. 24, No. 9, pp. 663-666.
Christopher J. Woolverton, "Toxicity of two carbamide peroxide products used in nightguard vital bleaching", *American Journal of Dentistry*, 1993, vol. 6, No. 6, pp. 310-314.
Van B. Haywood, "Response of normal and tetracycline-stained teeth with pulp-size variation to nightguard vital bleaching", *Journal of Esthetic Dentistry*, 1994, vol. 6, No. 3, pp. 109-114.
Ralph H. Leonard, et al, "Salivary pH changes during 10% carbamide peroxide bleaching" *Dental Research*, 1994, vol. 25, No. 8, pp. 547-550.
Ralph H. Leonard, et al, "Change in pH of plaque and 10% carbamide peroxide solution during nightguard vial bleaching treatment" *Esthetic Dentistry*, 1994, vol. 25, No. 12, pp. 819-823.
Van B. Haywood, "Historical development of whiteners: clinical safety and efficacy", *Aesthetics*, 1997, pp. 98-104.

Van B. Haywood, "Effectiveness, side effects and long-term status of nightguard vital bleaching", *JADA*, 1994, vol. 125, pp. 1219-1226.
James W. Curtis, et al, "Assessing the effects of 10 percent carbamide peroxide on oral soft tissues", *JADA*, 1996, vol. 127, pp. 1218-1223.
Fonda G. Robinson, et al, "Effect of 10 percent carbamide peroxide on color of provisional restoration materials", *JADA*, 1997, vol. 128, pp. 727-731.
Van B. Haywood, "Commonly asked questions about nightguard vital bleaching", *IDA Journal*, 1993, pp. 28-33.
Van B. Haywood, "Nightguard vital bleaching: current concepts and research", *JADA*, 1997, vol. 128, pp. 19s-25s.
Van B. Haywood, "Commonly asked questions about nightguard vital bleaching", *The Dental Assistant*, Mar./Apr. 1996, pp. 6-12.
M.S. McCracken, "Demineralization effects of 10 percent carbamide peroxide", *Journal of Dentistry*, 1996, vol. 24, No. 6, pp. 395-398.
Van B. Haywood, "Achieving, maintaining and recovering successful tooth bleaching", *Journal of Esthetic Dentistry*, 1996, vol. 8, No. 1, pp. 31-38.
Van B. Haywood, "Considerations and variations of dentist-prescribed, home-applied tooth-bleaching techniques", *Compound Educ Dent.*, 1994, Suppl. No. 17, pp. s616-s621.
Van B. Haywood, "Efficacy of six months of nightguard vital bleaching of tetracycline-stained teeth", *Journal of Esthetic Dentistry*, 1997, vol. 9, No. 1, pp. 13-19.
Carl M. Russell, et al, "Dentist-supervised home bleaching with ten percent carbamide peroxide gel: a six month study", *Journal of Esthetic Dentistry*, 1996, vol. 8, No. 4, pp. 177-182.
R.E. Goldstein, et al., "Chemistry of Bleaching", *Complete Dental Bleaching*, 1995, pp. 25-32 & 90-97, Quintessence Publishing Co., Inc.
Paul A. Sagel, et al., Vital Tooth Whitening With a Novel Hydrogen Peroxide Strip System: Design, Kinetics, and Clinical Response, Compendium, Supplement No. 29, vol. 21, 2000.
Office Action from the United States Patent & Trademark Office, dated Jun. 18, 2002, issued on U.S. Appl. No. 09/864,640, filed May 24, 2001, assignee—The Procter & Gamble Company, now abandoned.
Office Action from the United States Patent & Trademark Office, dated Sep. 5, 2002, issued on U.S. Appl. No. 09/864,686, filed May 24, 2001, assignee—The Procter & Gamble Company, now abandoned.
Office Action from the United States Patent & Trademark Office, dated May 28, 2003, issued on U.S. Appl. No. 09/864,686, filed May 24, 2001, assignee—The Procter & Gamble Company, now abandoned.
International Search Report, dated Sep. 24, 1998, issued on International Application No. PCT/US 98/11113.
International Search Report, dated Jan. 13, 1999, issued on International Application No. PCT/US 98/10967.
International Search Report, dated Apr. 14, 1999, issued on International Application No. PCT/US 98/17774.
International Search Report, dated Jul. 17, 2000, issued on International Application No. PCT/US 00/06604.
International Search Report, Jul. 26, 2000, issued on International Application No. PCT/US 00/06605.
International Search Report, dated Oct. 13, 2000, issued on International Application No. PCT/US 00/15891.
International Search Report, dated Oct. 13, 2000, issued on International Application No. PCT/US 00/18189.
International Search Report, dated Oct. 17, 2000, issued on International Application No. PCT/US 00/18187.
PCT Written Opinion, dated May 3, 2001, issue on International Application No. PCT/US00/18188.
International Preliminary Examination Report, dated Jul. 30, 2001, issued on International Application No. PCT/US00/18188.
International Search Report, dated Aug. 6, 2001, issued on International Application No. PCT/US 00/29384.
International Search Report, dated Apr. 5, 2002, issued on International Application No. PCT/US 01/19060.
International Search Report, dated Sep. 19, 2002, issued on International Application No. PCT/US 02/10630.

(56) References Cited

OTHER PUBLICATIONS

International Search Report, dated Oct. 9, 2002, issued on International Application No. PCT/US 01/24558.
Office Action from the United States Patent & Trademark Office, dated May 11, 2006, issued on U.S. Appl. No. 10/927,655, filed Aug. 26, 2004, assignee—The Procter & Gamble Company.
Office Action from the United States Patent & Trademark Office dated Nov. 30, 2006, issued on U.S. Appl. No. 10/927,655, filed Aug. 26, 2004, assignee—The Procter & Gamble Company.
Office Action from the United States Patent & Trademark Office dated Aug. 3, 2007, issued on U.S. Appl. No. 10/927,655, filed Aug. 26, 2004, assignee—The Procter & Gamble Company.
Office Action from the United States Patent & Trademark Office dated Apr. 17, 2008, issued on U.S. Appl. No. 10/927,655, filed Aug. 26, 2004, assignee—The Procter & Gamble Company.
Office Action from the United States Patent & Trademark Office dated Feb. 21, 2008, issued on U.S. Appl. No. 11/888,176, filed Jul. 31, 2007, assignee—The Procter & Gamble Company.
International Search Report, PCT/US 03/28612.
International Search Report, dated Sep. 25, 2003, issued on International Application No. PCT/US 03/16372.
International Search Report, dated Nov. 7, 2003, issued on International Application No. PCT/US 03/25354.
International Search Report, dated Jan. 7, 2004, issued on International Application No. PCT/US 03/26269.
International Search Report, dated Mar. 15, 2004, issued on International PCT/US2004/036322.
PCT Written Opinion, dated Mar. 21, 2005, issued on International Application No. PCT/ US2004/036322.
International Search Report, dated Oct. 31, 2006, issued on International Application No. PCT/US 06/019057.
Written Opinion of International Searching Authority dated Oct. 31, 2006, issued on International Application No. PCT/US2006/019057.
Declaration of Non-Establishment of International Search Report, dated Dec. 28, 2006, issued on International Application No. PCT/IB2006/05217.
Written Opinion of International Searching Authority dated Dec. 28, 2006, issued International Application No. PCT/IB2006/05217.
International Search Report, dated Feb. 18, 2008, issued on International Application No. PCT/IB2007/052834.
Written Opinion of International Searching Authority dated Feb. 18, 2008, issued on International Application No. PCT/IB2007/052834.
Newman, S.M. et al., "Tray—forming technique for Dentist—supervised home bleaching", Quintessence International, vol. 26, No. 7, pp. 447-453 (1995).
Messing, J.J., et al., Color Atlas of Endodontics, 1988, pp. 106-107, 135-140, 173-175, 257-259, The C.V. Mosby Company, Ltd.
Office Action from the United States Patent & Trademark Office dated Aug. 3, 2007, issued on U.S. Appl. No. 09/268,185, filed Mar. 15, 1999, assignee—The Procter & Gamble Company.
Office Action from the United States Patent & Trademark Office dated Sep. 24, 2002, issued on U.S. Appl. No. 09/268,185, filed Mar. 15, 1999, assignee—The Procter & Gamble Company.
Office Action from the United States Patent & Trademark Office dated Oct. 4, 2001, issued on U.S. Appl. No. 09/268,185, filed Mar. 15, 1999, assignee—The Procter & Gamble Company.
Office Action from the United States Patent & Trademark Office dated Oct. 20, 2001, issued on U.S. Appl. No. 09/864,640, filed May 24, 2001, 1999, assignee—The Procter & Gamble Company.
Office Action from the United States Patent & Trademark Office dated Jun. 18, 2002, issued on U.S. Appl. No. 09/864,640, filed May 24, 2001, 1999, assignee—The Procter & Gamble Company.
Office Action from the United States Patent & Trademark Office dated Jul. 1, 2004, issued on U.S. Appl. No. 10/321,252, filed Dec. 17, 2002, assignee—The Procter & Gamble Company.
Office Action from the United States Patent & Trademark Office dated Nov. 21, 2005, issued on U.S. Appl. No. 11/099,738, filed Apr. 6, 2005, assignee—The Procter & Gamble Company.
Office Action from the United States Patent & Trademark Office dated Jun. 29, 2006, issued on U.S. Appl. No. 11/157,769, filed Jun. 21, 2005, assignee—The Procter & Gamble Company.
Office Action from the United States Patent & Trademark Office dated Mar. 8, 2007, issued on U.S. Appl. No. 11/157,769, filed Jun. 21, 2005, assignee—The Procter & Gamble Company.
Office Action from the United States Patent & Trademark Office dated Sep. 25, 2007, issued on U.S. Appl. No. 11/157,769, filed Jun. 21, 2005, assignee—The Procter & Gamble Company.
Office Action from the United States Patent & Trademark Office dated Oct. 2, 2008, issued on U.S. Appl. No. 11/157,769, filed Jun. 21, 2005, assignee—The Procter & Gamble Company.
DC Chemical Co., Ltd., http://www.oci.co.kr/english/product/p_petr/p_petr8.htm pp. 1-10.
Dow Chemicals, http://www.dow.com/polyox/intro.htm pp. 1-2, Aug. 2002.

TOOTH WHITENING PRODUCT

FIELD OF THE INVENTION

The present invention relates to products for whitening teeth, and, more particularly, to products for whitening teeth that have a whitening agent incorporated therein.

BACKGROUND OF THE INVENTION

Tooth whitening has become very popular over the past few years. More and more consumers are choosing to whiten their teeth. Options for tooth whitening include toothpastes, mouthrinses, chewing gums, in-office bleaching, and most commonly tooth whitening solutions used with a tray obtained either over-the-counter or from a dentist. Tooth whitening products using a strip of material in combination with a chemical whitening active are known in the art. For example, U.S. Pat. No. 6,419,906, the substance of which is incorporated herein by reference, describes a tooth whitening product comprising a strip of material formed from a water hydratable polymer and a tooth whitening agent. While these whitening products may function for their intended purpose, there is continuing desire to improve the handling and aesthetics of these tooth whitening products.

SUMMARY OF THE INVENTION

A tooth whitening product is provided. The tooth whitening product has a backing layer and a tooth whitening composition. The tooth whitening composition includes first and second water soluble polymers, water, and a tooth whitening agent, wherein the first water soluble polymer is polyethelene oxide and the second water soluble polymer is polyvinyl alcohol.

BRIEF DESCRIPTION OF THE DRAWINGS

While the specification concludes with claims particularly pointing out and distinctly claiming the invention, it is believed that the present invention will be better understood from the following description taken in conjunction with the accompanying drawings in which:

DETAILED DESCRIPTION OF THE INVENTION

Figure 1:
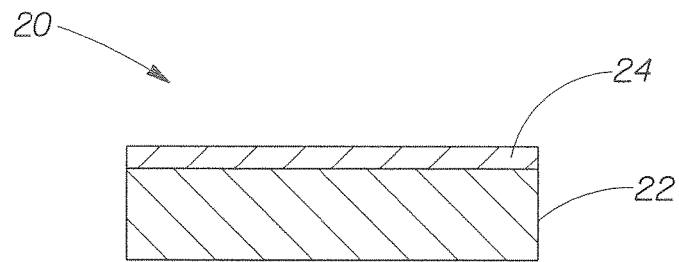
FIG. 1 is a cross-sectional side view of tooth whitening product made in accordance with the present invention, wherein a coating of a tooth whitening agent has been applied to a film.

All weight percentages herein refer to the tooth whitening composition after processing (e.g., after drying, cooling, curing, extrusion, or casting). Reference will now be made in detail to embodiments of the invention, examples of which are illustrated in the accompanying drawings wherein like numerals indicate the same elements throughout the views and wherein elements having the same two last digits (e.g., 20 and 120) connote similar elements. The present invention is directed to tooth whitening products comprising a tooth whitening composition including a tooth whitening or bleaching agent and one or more water soluble polymers and, optionally, water, and a plasticizer. In another embodiment, the invention is directed to a tooth bleaching composition comprising a tooth whitening agent and a polyethylene oxide polymer and a polyvinyl alcohol polymer. As used herein, the phrase "water soluble" preferably means a compound or composition whose solubility in water is greater than 5 wt %, preferably greater than 10 wt %, or more preferably greater than 15 wt % when measured in water at 20 C without the aid of pH adjusting agents, including solutes which are require temperatures greater than 20 C to solubilize in water but which still have the above-stated weight percentages when the solution is cooled to 20 C. Solubility is determined by More preferably, "water soluble" means a compound or composition whose solubility in water is greater than 5 wt %, preferably greater than 10 wt %, or more preferably greater than 15 wt % when first mixed in water at 20 C without the aid of pH adjusting agents. The water soluble polymers are also preferably water hydratable. As used herein, the phrase "water hydratable" is intended to refer to a compound or composition that absorbs water. While the present invention will be described herein with respect to these films or strips, it is contemplated that the present invention can be used with other tooth whitening products, such as dental trays. Water soluble polymers, which are also water hydratable, suitable for use with the present invention include ethylene oxide polymers, homopolymers or mixtures of ethylene oxide polymers of varying molecular weight ranging from about 10,000 Daltons and up to about 10,000,000 Daltons and preferably in the range of about 100,000 to about 1,500,000 Daltons. Such ethylene oxide polymers are commercially available from various sources. Polyethylene oxide in the molecular weight range of 10,000 to 1,000,000 Daltons is available from the Union Carbide Company under the tradename "Polyox". Other suitable polymers include polypropylene oxide, cross-linked polyacrylic acid, e.g., Carbopol, linear polyacrylic acid, polyvinyl alcohol, sodium alginate, methyl methacrylate, xanthan gum, pectin, pullulan, guar gum, agar, polyvinyl pyrolidone (PVP), carrageanan, celluloses (e.g., hydroxypropylcellulose, hydroxyethyl cellulose, hydroxypropylmethyl cellulose and hydroxymethyl cellulose), polyethylene oxide polypropylene oxide copolymers (e.g., poloxamer), microcrystalline cellulose, polyvinyl pyrolidone polyvinyl acetate copolymers, poly vinyl ester-methyl_copolymers, polyoxyethelene-polyoxypropylene block copolymer, and mixtures thereof. While the thickness of the film may vary, as described more fully hereafter, the film may have a thickness between about 0.1 micrometer and about 1500 micrometer (μm). The tooth whitening composition may be provided as a standalone film or may be applied to, coated on, or otherwise provided with a backing layer or strip of material. The backing layer can be provided as a single layer or as a laminate formed from a plurality of layers, such as any combination of a foam, mesh, or a strip of material. The backing layer can be water permeable, water impermeable, or partially water permeable. The backing layer can be continuous or discontinuous (i.e., formed from a plurality of discrete segments). Examples of some suitable backing layers are described in U.S. Pat. Nos. 5,891,453; 5,989,569; and 2004/0005277.

Hydration of the water soluble polymer by saliva in the oral cavity allows release (e.g., solubilizes, diffuses, or mobilizes) of the whitening agent incorporated in the polymer matrix. The whitening agent releases from the tooth whitening product to the tooth surfaces to which the tooth whitening composition is applied. Whitening or bleaching agents suitable for the practice of the present invention include peroxides, metal chlorites, perborates, percarbonates, peroxyacids, persulfates, and combinations thereof. Suitable peroxide compounds include hydrogen peroxide, urea peroxide, calcium peroxide, and mixtures thereof. Suitable metal chlorites include calcium chlorite, barium chlorite, magnesium chlorite, lithium chlorite, sodium chlorite, and potassium chlorite. The preferred chlorite is sodium chlorite. A preferred percarbonate is sodium percarbonate. Preferred persulfates are oxones.

Optionally, the water soluble polymer may be mixed with a plasticizer. Suitable plasticizers include glycols such as propylene glycol, polyethylene glycol, methoxypolyethylene glycol, polyhydric alcohols such as glycerin sorbitol, and xylitol, and glycerol esters such as glycerol triacetate. Glycerin can be used as well as propylene glycol or polyethylene glycol such as is available from Union Carbide Corporation as their series of Carbowaxes that range in molecular weight from 200 to 600 Daltons. Other plasticizers include cellulose esters, sebacate esters, castor oil, tricresyl phosphate, phthalate, adipate, ethyl citrate, ethanolamine, and oligosaccharides.

Optionally, any of the tooth whitening compositions described herein may further include an amount of water. The amount of water that is present may be varied by the amount of drying or curing that occurs. The embodiments of the present may include greater than about 2%, or about 4%, or about 6% or about 10% and/or less than about 90%, or about 40%, or about 30% of water by weight percent of the tooth whitening composition after drying.

In one embodiment of the present invention, a tooth whitening product 20 comprises a water soluble polymeric film 22 and a solid whitening agent that has been applied as a coating 24 to one side of the water soluble polymeric film 22, as shown in FIG. 1. The solid tooth whitening agent can be applied while the film is still tacky or after the film has dried, cured, or cooled. Application of the tooth whitening agent in this manner reduces exposure of the tooth whitening agent to any water that may have been used as a solvent in forming the film and also reduces the amount of contact between the water soluble polymer and the tooth whitening agent in comparison to a water hydratable film having a tooth whitening agent dispersed there throughout. In addition, this embodiment has an increased concentration of the tooth whitening agent at the surface that is applied to the teeth. Such a coating can also assist in the diffusion of the tooth whitening agent toward the tooth surface since the coating is directly adjacent and/or in contact with the tooth surface during use. Suitable solid tooth whitening agents that can be applied to one side of a water soluble polymeric film include carbimide peroxide, calcium peroxide, percarbonate, sodium percarbonate, perborates, persulfates, and mixtures thereof. These tooth whitening agents can be sprayed, applied by gravure printing, mist grinding, drop powdering, and other processes known in the art.

The coating of the solid tooth whitening agent can cover all or a portion of the water soluble polymeric film. The thickness of the coating can be greater than about 0.001 microns, or greater than about 0.005 microns, or greater than about 0.01 microns or greater than about 0.05 microns, or greater than about 0.1 microns, or greater than about 1 micron, or greater than 5 microns and/or less than about 100 microns, or less than about 50 microns, or less than about 10 microns, or less than about 1 micron. The dose per unit area of the tooth whitening agent is at least about $0.001$ mg/cm$^2$, or at least about $0.005$ mg/cm$^2$, or at least about $0.01$ mg/cm$^2$, or at least about $0.05$ mg/cm$^2$, or at least about $0.1$ mg/cm$^2$, or at least about $1$ mg/cm$^2$, or at least about $10$ mg/cm$^2$, or at least about $100$ mg/cm$^2$ and/or less than about $500$ mg/cm$^2$, or less than about $250$ mg/cm$^2$, or less than about $100$ mg/cm$^2$, or less than about $10$ mg/cm$^2$. Other materials can be mixed with the solid tooth whitening agent or applied sequentially before or after application of the solid tooth whitening agent. For example, binders, adherents, starches, sweeteners and flavorants, colorants (e.g., to aid in distinguishing the active side of the strip from the non-active side), release agents (e.g., talc powder, manitol powder, lecithin, corn oil, bees wax, silica, calcium monostearate, glycerol monostearate, alkali salts of long chain fatty acids) which facilitate release of the tooth whitening composition from a surface such as a casting plate, pH adjusting agents, including alkalizing agents or acidifying agents, surfactants (e.g., polysorbate 80 and glyceryl oleate), and other oral care actives can be applied as part of the application step. While the solid tooth whitening agent can be applied in a dry form, it is contemplated that a solvent could be used with the tooth whitening agent during application. In one embodiment, a solvent that solubilizes both the water soluble polymer and the tooth whitening agent can be employed when applying the tooth whitening agent to the surface of the water soluble film. In this process, the tooth whitening is solubilized in the solvent and then applied to the surface of the water soluble film so that the tooth whitening agent is dispersed at least partly within the film as the solvent can solubilize a portion of the film. Alternatively, the solvent may only solublize the tooth whitening agent, in which case a discrete coating would be formed on one side of the film after solvent evaporation or removal. Suitable solvents could include solvents that can solubilize the tooth whitening agent at a given temperature but which do not solubilize the water soluble polymer at that temperature. Some examples include Cellosolve acetate, anisole, 1,4 dioxane, ethyl acetate, ethylenediamine, dimethyl Cellosolve, Cellosolve solvent, alcohols such as ethanol, methanol, or iso-propanol, Carbitol solvent, n-butanol, cuyl Cellosolve, n-butyl acetate, 2-propanol, and methyl Cellosolve, and mixtures thereof.

The water soluble polymeric film 22 can be prepared using a conventional extrusion, calendaring, pressing or solvent casting processes. For example, to prepare a film by solvent casting polyethylene oxide, the ethylene oxide polymer or mixture of polymers is dissolved in a sufficient amount of a solvent which is compatible with the polymer. Examples of suitable solvents include water, alcohols, acetone, ethyl acetate or mixtures thereof. After a solution has been formed, a plasticizer is added with stirring, and heat is applied if necessary to aid dissolution, until a clear and homogeneous solution has been formed, followed by the addition of the whitening agent and any other ingredients such as flavors. The solution is coated onto a suitable carrier material and dried to form a film. The carrier material must have a surface properties that allow the polymer solution to spread evenly across the intended carrier width without soaking in to form a destructive bond between the two substrates. Examples of suitable carrier materials include glass, stainless steel, teflon, polyethylene-impregnated kraft paper. The solution can also be cast onto the previously described backing layers, a pouch or a portion of a package for the tooth whitening composition. Drying of the film may be carried out in a high-temperature air-bath using a drying oven, drying tunnel, vacuum drier, or any other suitable drying equipment, after which the tooth whitening agent can be sprayed onto the film.

In another embodiment of the present invention, the efficacy and/or stability of the tooth whitening agent can be increased by forming the water soluble film with a solvent other than water so that the tooth whitening agent does not come into contact with water during the formation process and there is no residual water left in the film post manufacture. As used herein, the term "stability" is intended to refer to the propensity of a material to maintain its original concentration or structure over a fixed period of time. As used herein, the term "efficacy" is intended to refer to the amount of tooth whitening per unit time. In one process, the water soluble polymer and the tooth whitening agent are mixed and then fed to an extruder whose screw, through mechanical action, melts the water-hydatratable polymer. The melted polymer is then extruded into a film to be formed into the tooth whitening product.

The efficacy of the tooth whitening agent can also be increased by reducing the amount of water soluble polymer that forms the film. In one embodiment, the water soluble polymer film further comprises water insoluble organic and/or inorganic additives to reduce the amount of the water soluble polymer so that solubilization of the tooth whitening agent is maximized during use. Suitable water insoluble organic materials include polyolefins (e.g., polyethylene, polypropylene, polybutenes, polyisoprenes, and copolymers thereof) and polyester. Suitable water insoluble inorganic materials include calcium phosphate, calcium pyrophosphate, and titanium dioxide, and silica. The water insoluble additives can comprise at least about 10%, or at least about 20%, or at least about 30% and/or less than about 90%, or less than about 80%, or less than about 70%, or less than about 50% or less than about 40%, or less than about 30% by weight of the film. In these embodiments, the amount of the water soluble polymer is at least about 5%, or at least about 10%, or at least about 20%, or at least about 30% and/or less than about 90%, or less than about 80%, or less than about 70% by weight of the film. The water insoluble additives can be ground prior to incorporation into the film. In one embodiment, the average particle size of the water insoluble additives is at least about 1 micron, or at least about 20 microns, or at least about 25 microns and/or less than about 100 microns, or less than about 50 microns, or less than about 25 microns, or less than about 10 microns. In addition to decreasing the amount of water soluble polymer that is available to react with the tooth whitening agent, the concentration of tooth whitening agent available at the surface of the tooth can be increased during hydration, because more water is available to solubilize the tooth whitening agent rather than hydrating or otherwise solubilizing the water soluble polymer. The tooth whitening agent can be admixed with the water soluble polymer as described in U.S. Pat. No. 6,419,906 or coated onto the film as previously described.

Figure 2:
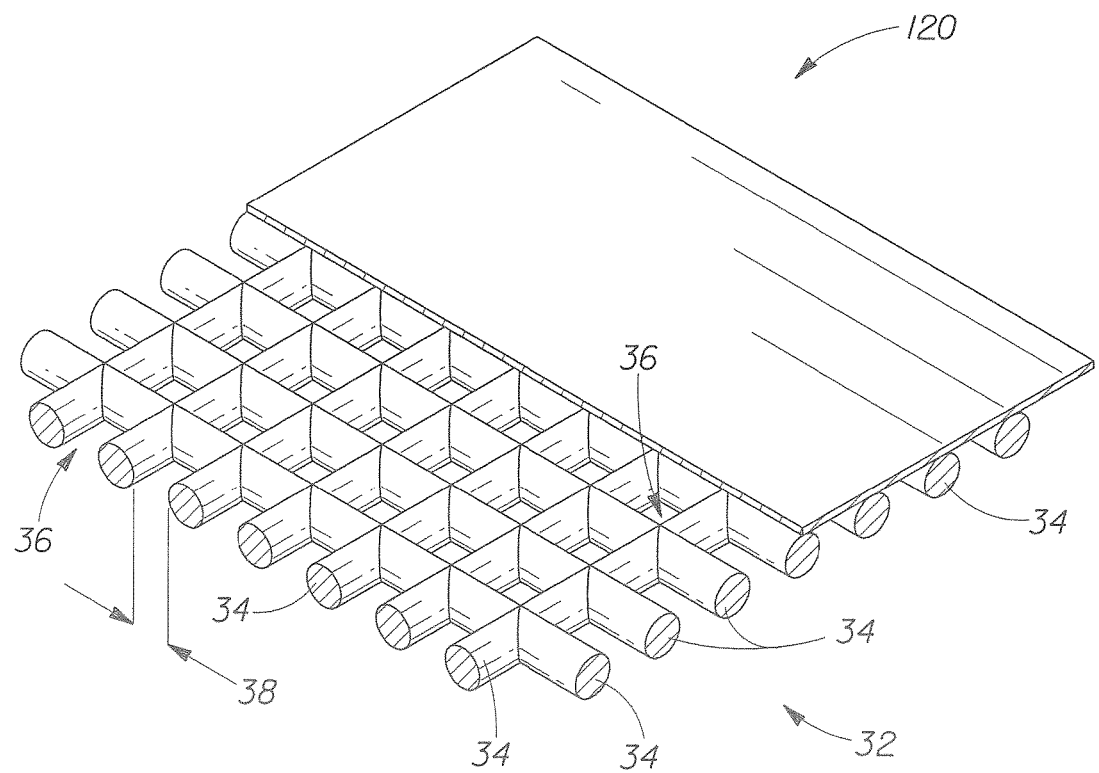
FIG. 2 is a perspective view of another embodiment of a tooth whitening product of the present invention, wherein the tooth whitening product comprises a web and a coating that completely bridges the void spaces of the web and wherein a portion of the coating has been removed to reveal features there below.

In yet another embodiment of the present invention, a web, scrim, or mesh is incorporated in the tooth whitening product to improve the hydration of the film. The web, scrim, or mesh can be formed from fibers that are aligned in random or repeating geometric patterns. Referring to FIG. 2, a tooth whitening product 120 comprising a web 32 is illustrated. The web 32 is formed from fibers 34 that are arranged in a repeating geometric pattern. The fibers can be formed from one or more water insoluble, water soluble, or water hydratable polymers and may have a tooth whitening agent incorporated therein. If the fibers are formed from water insoluble materials, the web may function in a manner similar to the previously described films that incorporate water insoluble materials. The fibers are arranged in a manner to provide void spaces 36 between the fibers. The void spaces can facilitate hydration of the web 32 and therefore solubilization of the tooth whitening agent. The void spaces can vary in size or have a substantially constant size over the web. For example, the void spaces might be smaller in one region and larger in another region depending upon the desired rate of hydration. The fibers 34 can have a diameter of at least about 1 micron, or at least about 5 microns, or at least about 10 microns, or at least about 20 microns, or at least about 50 microns and/or less than about 200 microns, or less than about 100 microns, or less than about 50 microns, or less than about 20 microns. The spacing 38 between fibers is at least about 1 micron, or at least about 5 microns, or at least about 10 microns, or at least about 20 microns, or at least about 50 microns, or at least about 1 mm, or at least about 1.5 mm and/or less than about 5 mm, or less than about 2.5 mm, or less than about 1.5 mm, or less than about 50 microns.

Figure 3:
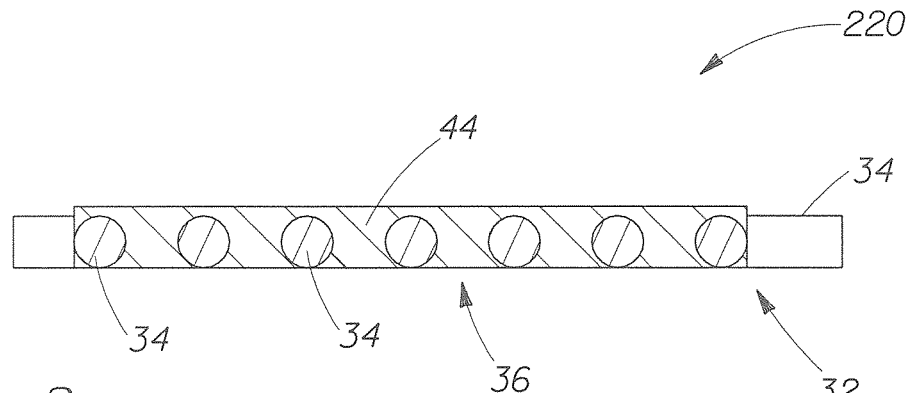
FIG. 3 is a cross-sectional side view of the tooth whitening product of FIG. 2, wherein the void spaces are shown as partially filled.
Figure 4:
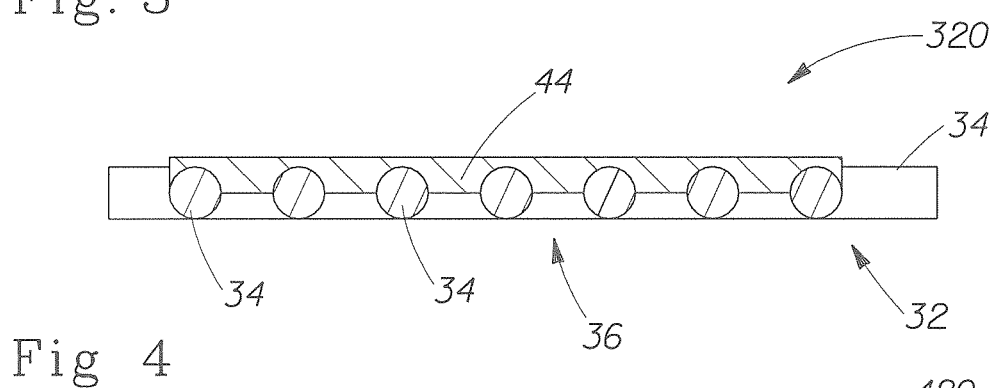
FIG. 4 is a cross-sectional side view of the tooth whitening product of FIG. 2, wherein the void spaces are shown as completely filled.
Figure 5:
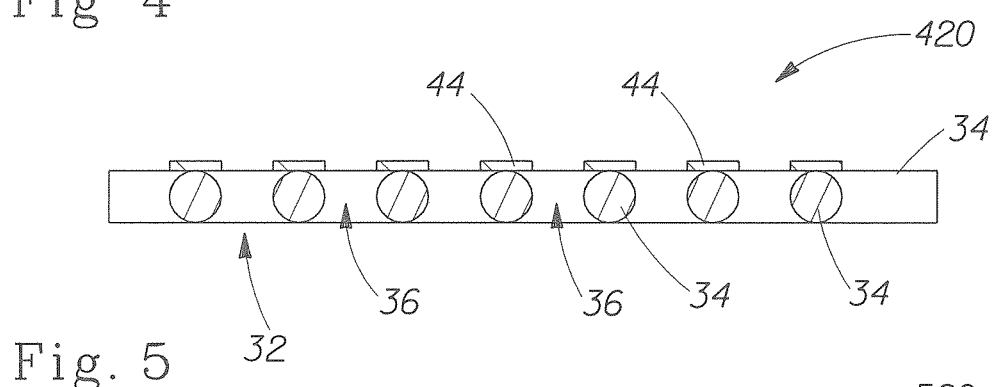
FIG. 5 is a perspective view of another embodiment of a tooth whitening product of the present invention, wherein the tooth whitening product comprises a web and a coating that partially bridges the void spaces of the web.
Figure 6:
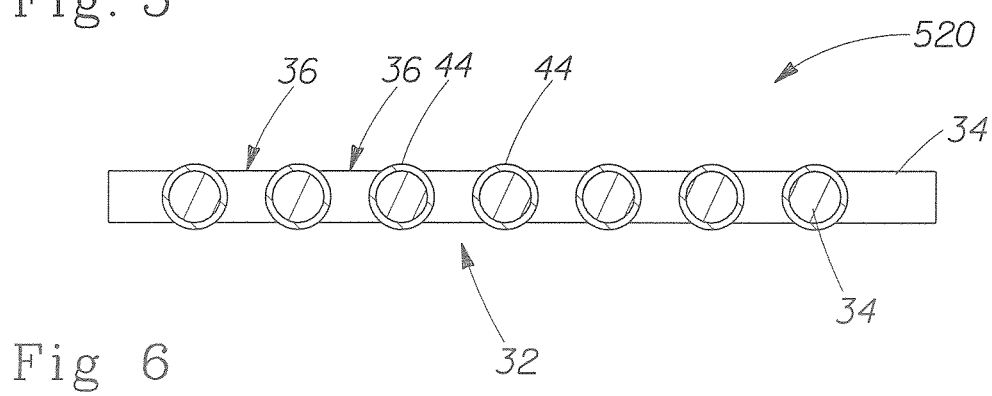
FIG. 6 is a perspective view of another embodiment of a tooth whitening product of the present invention, wherein the tooth whitening product comprises a web and a coating that does not bridge the void spaces of the web.

In an alternate embodiment, a tooth whitening product 220, shown in FIG. 3, comprises a web 32 having a coating or layer 44 applied thereto. The web 32 can be formed a water soluble, water insoluble, or water hydratable polymer or other material, such as other polymers (e.g., polypropylene, polyethylene, etc.) and cellulose. The fibers 34 of the web 32 can be arranged in a random or repeating pattern. The coating 44 comprises a water soluble polymer and a tooth whitening agent. Other materials can be included in the coating, such as a plasticizer, water, water insoluble additives, etc. The coating can bridge the void spaces 36 such that a substantially solid layer is formed on web 32. The coating might completely fill the void spaces as shown in FIG. 3 or partially fill the void spaces as shown in FIG. 4 with respect to tooth whitening product 320. When the void spaces are partially filled, the pocket 50 that is formed can facilitate hydration of the web and therefore solubilization and release of the tooth whitening agent. Alternatively, the coating 44 can only partially bridge the void spaces, as shown in FIG. 5 for the tooth whitening product 420. In yet another embodiment, a coating 44 does not bridge the void spaces 36 of web 32 but merely coats the fibers 34, either wholly or partially, as shown by way of example in FIG. 6 for the tooth whitening product 520.

The concentration of the tooth whitening agent within the coating and/or the fibers and the amount of water soluble polymer can be varied within these web embodiments depending upon the extent to which the coating bridges the void spaces and/or coats the fibers and based upon the desired rate of solibilization of the tooth whitening agent. As will be appreciated, any combination of completely filling the voids, partially filling the voids, partially bridging the voids, and coating the fibers can be provided in one embodiment.

Figure 7:
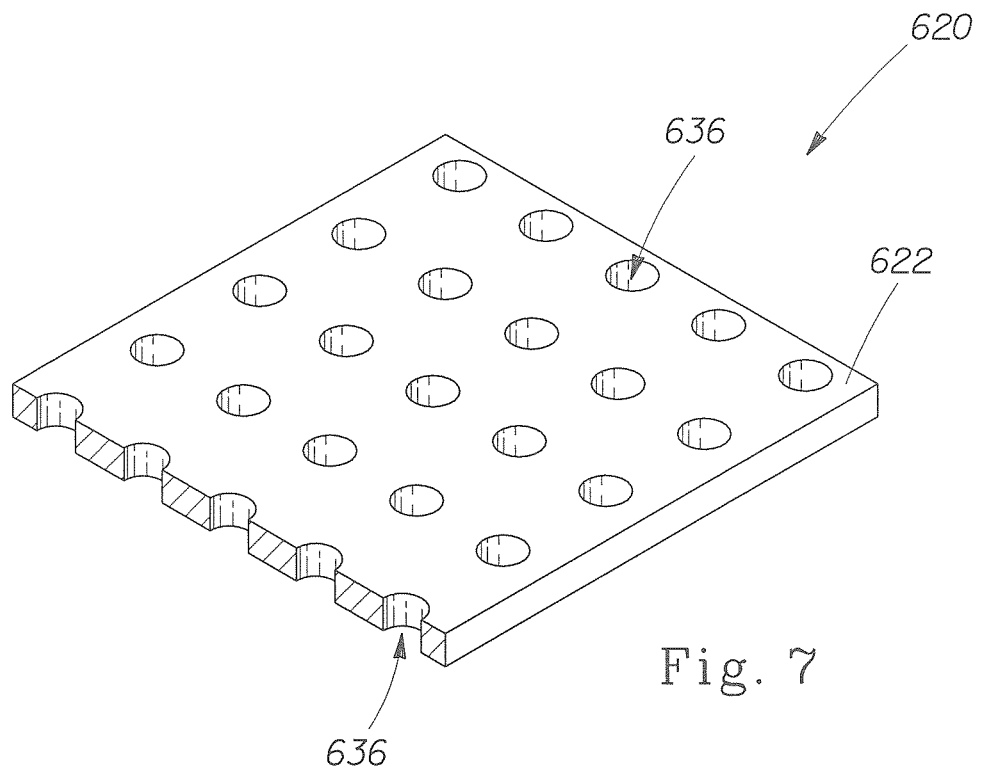
FIG. 7 is a cross-sectional side view of another embodiment of a tooth whitening product of the present invention that comprises a perforated film.

In a related embodiment, a perforated film without a distinct web or scrim might be provided, as shown in FIG. 7. In the tooth whitening product 620, a single or multilayer film might be provided comprising a water soluble polymer, a tooth whitening agent, a plasticizer, and optionally water. The film can be perforated after it has dried or cured. The void spaces, holes, or apertures 630 that are formed during the perforation process can pass completely through the thickness of the film or might only partially penetrate the film thickness. The void spaces 636 can have the same dimensions as previously described with respect the void spaces of the web. The void spaces 636 can be provided in a random or repeating pattern and vary in size and shape as previously described. Further, this embodiment can include a coating of a tooth whitening agent as previously described or other features of the embodiments discussed above.

Figure 8:
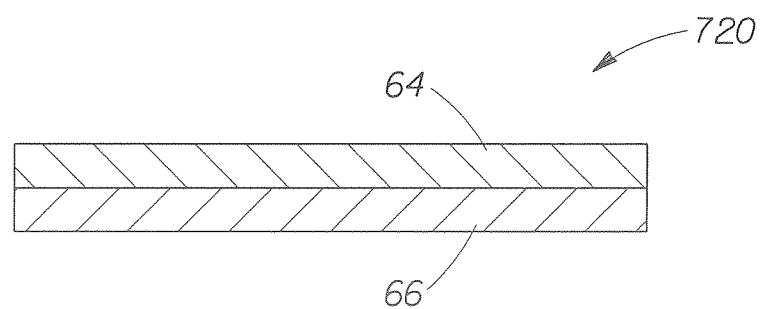
FIG. 8 is a perspective view of another embodiment of a tooth whitening product of the present invention that comprises a first layer and a second layer.

In another embodiment of the present invention, a tooth whitening product 720 is provided in the form of a laminated film as shown in FIG. 8. The laminated film comprises two or more layers comprising water hydratable polymers. A first layer 64, which is to be applied to the teeth, further comprises a tooth whitening agent. The water hydratable polymer comprises at least about 1%, or at least about 10%, or at least about 20% and/or less than about 90%, or less than about 70%, or less than about 50% by weight of the first layer. The tooth whitening agent comprises at least about 1%, or at least about 10%, or at least about 15% and/or less than about 70%, or less than about 60%, or less than about 50% by weight of the first layer. The balance of the first layer can comprise water or other materials, such as the previously described water insoluble additives or a plasticizer. The second layer 66, which is positioned adjacent the lips and/or cheeks during use, preferably does not comprise a tooth whitening agent. The water hydratable polymer of the second layer 66 comprises at least about 20%, or at least about 30%, or at least about 40% and/or less than about 100%, or less than about 90%, or less than about 80% by weight of the second layer. A plasticizer comprises at least about 0.1%, or at least about 1%, or at least about 2% and/or less than about 40%, or less than about 30%, or less than about 20% by weight of the second layer. The balance of the second layer 66 can comprise other materials, such as water, water insoluble additives, or oral care actives other than a tooth whitening agent. Examples of other oral care actives suitable for use with the present invention include phosphates (e.g., pyrophosphates, polyphosphate, polyphosphonates, and mixtures thereof), fluoride ion sources, antimicrobial agent, anti-imflamatory agents, nutrients, and enzymes. These oral care actives are further described in U.S. Pat. No. 6,096,328 (and the patents cited therein), the substances of which are incorporated herein by reference. These other oral care actives could also be incorporated into a film comprising only a single layer and formed from a water-hydratable polymer (e.g., polyethyylene oxide) and a plasticizer, the basic formation of which is described in U.S. Pat. No. 6,419,906.

The composition of the first layer 64 and the second layer 66 of the tooth whitening product 720 can be adapted to provide different functionalities. For example, the first layer 64 might comprise less of the water hydratable polymer than the second layer 66 so that the first layer 64 hydrates more quickly thereby solubilizing the tooth whitening agent more quickly and more effectively (i.e., providing a greater concentration more quickly). The second layer can contain relatively more of the water hydratable polymer so that it functions as a barrier layer preventing diffusion of the solubilized tooth whitening agent away from a tooth while still permitting some hydration from the back side of the tooth whitening product. Also, since the second outer layer comprises more of the water soluble polymer, it will remain in a film-like state longer than the first layer 64 so that the tooth whitening agent will have a longer period of time in which to act upon the teeth. The absence of the tooth whitening agent from the second layer could also improve tissue tolerablity as a peroxide source would not be directly adjacent the soft tissue of the lips and cheeks. The tooth whitening product 720 can be formed by casting the first layer first followed by the second layer being cast on top of the first layer either before or after the first layer has dried or cured. The layers can be pressed together by rollers aligned so that there is nip of gap there between through which the first and second layers pass. The first and second layers can comprise the same water soluble polymer or distinct water soluble polymers.

In another aspect of the present invention, a film comprising a water soluble polymer and a tooth whitening agent is provided in a thin form and with an increased concentration of the tooth whitening agent. The thickness of the film is at least about 1 µm, or at least about 5 µm, or at least about 10 µm, or least about 15 µm and/or less than about 2 mm, or less than about 1 mm, or less than about 0.5 mm, or less than about 0.25 mm, or less than about 0.1 mm, or less than about 20 µm, or less than about 15 µm. The concentration of the tooth whitening agent is at least about 1%, or at least about 10% or at least about 15%, or at least about 20%, or least about 25% and/or less than about 70%, or less than about 60%, or less than about 50%, or less than about 40%, or less than about 30%. Surprisingly, these increased concentration levels of the tooth whitening agent can be utilized while still maintaining acceptable soft tissue tolerability without the need for cumbersome rubber dams or other artificial soft tissue barriers. As used herein, the phrase "artificial barrier" is intended to refer to any physical means that prevents or is intended to prevent a tooth whitening agent from migrating onto the soft tissue adjacent the teeth during a bleaching operation. Other artificial barriers can include light cured resins. As used herein, the phrase "soft tissue tolerability" is intended to refer to the degree to which a user experiences a sensation often described as burning or stinging or experiences irritation of the gingival tissues. This sensation can range from minor to severe. In addition, one or more layers, preferably without a tooth whitening agent, can be provided adjacent the previously described layer containing the tooth whitening agent.

In another embodiment, the tooth whitening composition comprises two or more water soluble polymers, a tooth whitening agent, and optionally a plasticizer, and/or water. The tooth whitening composition may be provided as a layer on a backing layer, as as a stand-alone film, or in other forms. In a preferred embodiment, the first water soluble polymer is a polyethylene oxide polymer and the second water soluble polymer is polyvinyl alcohol. The polyethylene oxide may have an average molecular weight greater than about 100,000, or about 200,000, or about 300,000, or about 600,000 and or less than about 10,000,000, or about 4,000,000, or about 1,500,000, or about 900,000. The tooth whitening composition may comprise greater than about 10%, or about 20%, or about 30% or about 40% and/or less than about 90%, or about 60%, or about 50% by weight of polyethylene oxide. The tooth whitening composition may comprise mixtures of polyethylene oxides have different average molecular weights. The tooth whitening composition may comprise greater than about 0.5%, or about 2%, or about 5% and/or less than about less than about 90% or about 50%, or about 20%, or about 15% or about 10% by weight of polyvinyl alcohol. The ratio of the first water soluble polymer to the second water soluble polymer is between about 10:90 and about 90:0.5 or between about 50:2 and about 30:20. The polyvinyl alcohol may have varying degrees of hydrolysis. The degree of hydrolysis signifies the extent of conversion of polyvinyl acetate to polyvinyl alcohol. A mixture of polyethylene oxide and polyvinyl alcohol will be more adhesive and less cohesive as the degree of hydrolysis of the polyvinyl alcohol increases. Thus, for the same amount of polyethylene oxide, less polyvinyl alcohol is required as the degree of hydrolysis of the polyvinyl alcohol increases in order to provide the same level of adhesiveness. The polyvinyl alcohol may be super hydrolyzed, fully hydrolyzed, intermediately hydrolyzed, or partially hydrolyzed. Typically, the range of hydrolysis, from partially hydrolyzed to super hydrolyzed, is between about 70% (partially hydrolyzed) and about 99.5% (super hydrolyzed). In one embodiment, the range of hydrolysis is greater than about 70%, or about 80%, or about 87% and/or less than about 99%, or about 95%, or about 91%. As used herein, the phrase "hydrolysis" is intended to refer to the level of hydrolysis of the raw material before manufacture of the tooth whitening composition. In another embodiment, the range of hydrolysis is between about 87% and about 91% and the amount of polyvinyl alcohol between about _5_% and about _50_% by weight of the tooth whitening composition. The tooth whitening composition may also optionally include a plasticizer. In one embodiment, the tooth whitening composition may comprise greater than about 1%, or about 10%, or about 20% and/or less than about 80%, or about 60%, or about 80% by weight of a plasticizer. A preferred plasticizer is polyethylene glycol. A more preferred plasticizer is a polyethylene glycol having a molecular weight between about 200 and about 9,000. The tooth whitening composition may also optionally include water at the same levels as previously discussed herein. The tooth whitening composition. The tooth whitening composition may include hydrogen peroxide greater than about 0.5%, or about 3%, or about 6% and/or less than about 40%, or about 20%, or about 10% by weight of the tooth whitening composition. The foregoing embodiments of a tooth whitening composition comprising two water soluble polymers may also incorporate aspects of any of the other embodiments described herein, such as a mesh or scrim, water insoluble organic or inorganic additives, perforations, etc.

Non-limiting examples of the foregoing embodiments incorporating a mixture of polyethylene oxide and polyvinyl alcohol are set forth below. It will be appreciated that these compositions may include additional ingredients or other ingredients may be substituted for those listed. Each example sets forth the tooth whitening composition formulation before drying and after drying.

EXAMPLE 1

|  | Polyethylene oxide WSR-1105 (MW 900,000) | Polyvinyl alcohol Gohsenol GL-05S (86.5%-89%) | PEG 600 | Water | Hydrogen peroxide |
| --- | --- | --- | --- | --- | --- |
| % wt before drying | 6 | 2 | 6.5 | 82.5 | 3 |
| % wt after drying | 30 | 10 | 35 | 10 | 15 |

EXAMPLE 2

|  | Polyethylene oxide WSR-205 (MW 600,000) | Polyvinyl alcohol Gohsenol NH-26 (99.4%) | PEG 600 | Water | Hydrogen peroxide |
| --- | --- | --- | --- | --- | --- |
| % wt before drying | 7.5 | 0.5 | 5 | 85 | 2 |
| % wt after drying | 40 | 2.5 | 25 | 22.5 | 10 |

EXAMPLE 3

|  | Polyethylene oxide WRS-1105 (MW 900,000) | Polyvinyl alcohol Gohsenol KH-17 (78.5-81.5%) | PEG 600 | Water | Hydrogen peroxide |
| --- | --- | --- | --- | --- | --- |
| % wt before drying | 4 | 5 | 6 | 84 | 1 |
| % wt after drying | 20 | 25 | 30 | 19 | 6 |

EXAMPLE 4

|  | Polyethylene oxide WSR-N750 (MW 300,000) | Polyvinyl alcohol Gohsenol GL-05S (86.5-89%) | PEG 600 | Water | Hydrogen peroxide |
| --- | --- | --- | --- | --- | --- |
| % wt before drying | 6.5 | 3 | 6 | 81.5 | 3 |
| % wt after drying | 34 | 15 | 30 | 6 | 15 |

Embodiments of the polyethylene oxide/polyvinyl alcohol mixtures of the present invention, including examples 1 to 4, can be made by preparing a first mixture comprising polyethylene oxide and a solvent, such as water, and a second mixture comprising polyvinyl alcohol and a solvent, such as water. It will be appreciated that a mixture of solvents might also be used herein. Both mixtures are separately stirred until both the polyethylene oxide and the polyvinyl alcohol are fully hydrated. The first and second mixtures are combined and a tooth whitening agent (e.g., hydrogen peroxide) and optionally a plasticizer (e.g., PEG 600) are added. This tooth whitening composition may be cast on a backing layer or a suitable drying surface. The tooth whitening composition is then dried until a desired amount of the solvent has been removed. The tooth whitening composition can be freeze dried or a drying tunnel incorporating radiant or convective heating can be used. In one embodiment, the tooth whitening composition can be dried in drying box using a nitrogen air mixture at room temperature at a flow rate between about 0.085 m$^3$/min and about 0.3 m$^3$/min. The drying time may be between about 15 minutes and about 2 hours or between about 20 minutes and about 60 minutes.

The above described embodiments of the present invention can be further combined with other layers such as a thin protective coating layer, e.g., of 10 nanometers (nm) to 500 microns (um) thickness or a backing layer formed from a strip of material. The coating material is applied in a sufficiently thin layer so as not to interfere with the flexibility of the film and to allow the whitening strip to conform to an arrangement of a row of teeth. The coating materials can be one or a combination of high molecular weight (that is, molecular weights greater than 1,000,000 Dalton) and include, ethyl cellulose, propyl cellulose, isopropyl cellulose, butyl cellulose, t-butyl cellulose, cellulose acetate, and derivatives of polyvinyl alcohol such as polyvinyl acetate and shellac.

The tooth whitening products of the present invention can be packaged in pouches as individual strips or a roll of film can be provided in a tape-like dispenser, wherein individuals strips can be cut from the roll for use in the oral cavity or the film can be provided with perforations or other frangible features to permit separation of predetermined length strips from the roll of film. Optionally, the tooth whitening products of the present invention can further include a release liner. The release liner can be formed from any material that exhibits less affinity for the film and/or web than the film or web exhibits for itself. The release liner can be formed from polymer films, paper, foils, woven, non-wovens, and other suitable materials known in the art. Optionally, the release liner can include a coating such as wax, silicone, Teflon®, fluoropolymers, etc. The films of the present invention can be formed directly on the release liner. The release liner can be cut to the desired size either before or after formation of the film thereupon. The tooth whitening products of the present invention can also be provided as liner for dental trays, such as those described in U.S. Pat. No. 5,098,303, wherein the strips are incorporated into the trough of the dental tray.

To use the tooth whitening products of the present invention, the film when applied to the teeth surface when hydrated by saliva in the oral cavity or prewetted by dipping the strip in water will adhere to the teeth in an appropriate manner. In this regard, the tooth whitening product is formed to have a width dimension suitable to cover a row of teeth (upper or lower). Therefore, the tooth whitening product may be applied to the upper set of teeth, or to the lower set of teeth either separately or simultaneously. The length dimension of the tooth whitening product is determined by the amount of coverage desired. In this regard, the number of teeth which it is desired to whiten will determine the dimensions of the product. For instance, it may be desired to only whiten the front teeth, which are most easily seen by others. Accordingly, the length of tooth whitening product can be reduced in this case, as compared to the case where it is desired to whiten all of the teeth. The duration of application of product to the teeth will depend upon the type and concentration of the tooth whitening agent, as well as the type and intensity of extrinsic or intrinsic stain.

The embodiments described herein were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A tooth whitening product, comprising:
   a first layer comprising a tooth whitening composition comprising first and second polymers, water, and a tooth whitening agent, wherein said first polymer is polyethylene oxide with an average molecular weight of from about 300,000 to about 900,000 and said second polymer is polyvinyl alcohol, wherein the first layer contacts at least one tooth;
   a second layer that does not comprise a tooth whitening agent.

2. The tooth whitening product of claim 1, wherein the concentration of said first polymer is between about 10% and about 90% by weight of said tooth whitening composition.

3. The tooth whitening product of claim 1, wherein the concentration of said second polymer is between about 0.5% and about 50% by weight of said tooth whitening composition.

4. The tooth whitening product of claim 1, wherein the concentration of said water is between about 2% and about 90% by weight of said tooth whitening composition.

5. The tooth whitening product of claim 1, wherein said tooth whitening composition further comprises a plasticizer having a concentration between about 1% and about 80% by weight of said tooth whitening composition.

6. The tooth whitening product of claim 5, wherein said plasticizer is polyethylene glycol.

7. The tooth whitening product of claim 1, wherein said polyvinyl alcohol has a hydrolysis between about 70% and about 91%.

8. The tooth whitening product of claim 1, wherein the second layer is a laminate.

9. The tooth whitening product of claim 1, wherein said tooth whitening composition comprises a mixture of two or more polyethylene oxides and wherein said polyethylene oxides have different average molecular weights.

10. The tooth whitening product of claim 1, wherein said tooth whitening agent of the first layer is hydrogen peroxide.

11. The tooth whitening product of claim 1, wherein said first and second polymers are water soluble.

12. The tooth whitening product of claim 1, wherein the second layer comprises at least about 20%, by weight of the second layer, of a water hydratable polymer.

13. The tooth whitening product of claim 12, wherein the water hydratable polymer is polyethylene oxide with an average molecular weight of from about 300,000 to about 900,000.

14. The tooth whitening product of claim 13, wherein there is more polyethylene oxide in the second layer than in the first layer, by total weight of the tooth whitening product.

15. The tooth whitening product of claim 1, wherein the second layer comprises an oral care active other than the tooth whitening agent.

* * * * *